(12) United States Patent
Wik et al.

(10) Patent No.: US 10,022,295 B2
(45) Date of Patent: Jul. 17, 2018

(54) CHEST COMPRESSION DEVICE

(71) Applicant: OSLO UNIVERSITETSSYKEHUS HF, Nydalen (NO)

(72) Inventors: Lars Wik, Oslo (NO); Morten Eriksen, Oslo (NO); Jo Kramer Johansen, Oslo (NO); Petter Andreas Steen, Oslo (NO); Kjetil Sunde, Oslo (NO)

(73) Assignee: OSLO UNNIVERSITETSSYKEHUS HF, Nydalen (NO)

( * ) Notice: Subject to any disclaimer, the term of this patent is extended or adjusted under 35 U.S.C. 154(b) by 439 days.

(21) Appl. No.: 14/434,490

(22) PCT Filed: Oct. 11, 2013

(86) PCT No.: PCT/EP2013/071344
§ 371 (c)(1),
(2) Date: Apr. 9, 2015

(87) PCT Pub. No.: WO2014/057116
PCT Pub. Date: Apr. 17, 2014

(65) Prior Publication Data
US 2015/0272822 A1    Oct. 1, 2015

(30) Foreign Application Priority Data
Oct. 12, 2012 (GB) .................................. 1218336.4

(51) Int. Cl.
*A61H 31/00* (2006.01)
*A61H 9/00* (2006.01)
*A61N 1/39* (2006.01)

(52) U.S. Cl.
CPC ......... *A61H 31/007* (2013.01); *A61H 9/0078* (2013.01); *A61H 31/006* (2013.01);
(Continued)

(58) Field of Classification Search
CPC .... A61H 31/00; A61H 31/004; A61H 31/005; A61H 31/006; A61H 31/007; A61H 31/008; A61H 2201/1246
See application file for complete search history.

(56) References Cited

U.S. PATENT DOCUMENTS 2,071,215 A * 2/1937 Petersen ................ A61H 31/00
128/DIG. 10
3,291,124 A * 12/1966 Jennings ............... A61H 31/006
601/106

(Continued)

FOREIGN PATENT DOCUMENTS

| JP | 2000024069 A | 1/2000 |
| WO | 94/20060 A1 | 9/1994 |

(Continued)

*Primary Examiner* — Justine Yu
*Assistant Examiner* — Christopher Miller
(74) *Attorney, Agent, or Firm* — Lane Powell PC

(57) ABSTRACT

A chest compression device for cardiopulmonary resuscitation may include a support structure for placement about a patient's chest and for holding a chest compressor above a patient's sternum; a chest compressor mounted on the support structure; and lateral chest supports attached to the support structure at points laterally on either side of the chest when the device is in use, such that the lateral chest supports will apply lateral pressure to the sides of the chest synchronised with a chest compression by the chest compressor.

21 Claims, 4 Drawing Sheets

(52) U.S. Cl.
CPC ..... *A61H 31/008* (2013.01); *A61H 2031/002* (2013.01); *A61H 2031/003* (2013.01); *A61H 2201/0214* (2013.01); *A61H 2201/0242* (2013.01); *A61H 2201/0278* (2013.01); *A61H 2201/10* (2013.01); *A61N 1/39* (2013.01)

(56) References Cited

U.S. PATENT DOCUMENTS

| | | | |
|---|---|---|---|
| 3,425,409 A | | 2/1969 | Isaacson et al. |
| 3,782,371 A | * | 1/1974 | Derouineau ......... A61H 31/007 601/105 |
| 5,473,864 A | | 12/1995 | Scott |
| 5,490,820 A | * | 2/1996 | Schock ................ A61H 9/0078 601/1 |
| 5,575,027 A | | 11/1996 | Mueller |
| 5,743,864 A | | 4/1998 | Baldwin, II |
| 6,682,552 B2 | * | 1/2004 | Ramsden ................ A61F 7/10 607/109 |
| 2002/0026131 A1 | * | 2/2002 | Halperin .............. A61H 9/0078 601/41 |
| 2003/0181834 A1 | * | 9/2003 | Sebelius .............. A61H 31/008 601/41 |
| 2004/0073580 A1 | | 4/2004 | Nakayama et al. |
| 2004/0162587 A1 | | 8/2004 | Hampton et al. |
| 2004/0181179 A1 | * | 9/2004 | Hwang ................ A61H 31/006 601/44 |
| 2008/0114406 A1 | | 5/2008 | Hampton et al. |
| 2009/0020129 A1 | * | 1/2009 | Shaffer ................ A61H 31/006 128/845 |
| 2009/0093741 A1 | * | 4/2009 | Lach .................... A61H 31/005 601/41 |
| 2009/0187123 A1 | * | 7/2009 | Hwang ................ A61H 31/006 601/41 |
| 2011/0295163 A1 | * | 12/2011 | Vijayanagar ............... A61F 7/02 601/18 |
| 2012/0116272 A1 | | 5/2012 | Hampton et al. |
| 2013/0030333 A1 | * | 1/2013 | Cicenas ................ A61H 31/005 601/41 |

FOREIGN PATENT DOCUMENTS

| | | |
|---|---|---|
| WO | 2007050424 A2 | 5/2007 |
| WO | 2010/119401 A1 | 10/2010 |
| WO | 2012/038855 A1 | 3/2012 |

* cited by examiner

CHEST COMPRESSION DEVICE

TECHNICAL FIELD

The invention relates to a chest compression device for use in cardiopulmonary resuscitation (CPR) and to a method of chest compression in cardiopulmonary resuscitation.

BACKGROUND OF THE INVENTION

Sudden cardiac arrest (SCA) outside the hospital is a leading cause of death in the western world, and globally the incidence is estimated to 55 per 100 000 person-years. The number of patients surviving to hospital discharge remains low. A recent meta-analysis stated the aggregate survival rate to hospital discharge to be 7.6%, which has not significantly changed in almost 30 years.

Chest compression during cardiopulmonary resuscitation (CPR) remains one of few proven treatments for patients suffering from sudden cardiac arrest, supplying blood to the critical organs—brain and heart-muscle—until spontaneous circulation hopefully resumes. It has been shown that a higher quality of CPR improves the outcome. In both experimental and clinical studies chest compressions before defibrillation attempts increase the chance both of successful defibrillation and survival. The compression profile (how rapidly the chest is compressed and decompressed), frequency, depth and duty cycle of the chest compressions affect the blood flow and pressures obtained during CPR.

The quality of CPR can now be measured by accelerometers and transthoracic impedance, and the quality of manual CPR given by professionals has been found to be substantially below international recommendations. Mechanical chest compression devices have the potential to improve these factors. They can give consistent chest compressions, can free the personnel to accomplish other chores and can be used during transport where high quality manual compressions are impossible and are dangerous for the medical personnel who in that case cannot be belted in the vehicle. Chest compression devices can also enable chest compressions during interventions on the coronary arteries in the catheter laboratory. The ideal function and properties of such devices are far from determined at present.

There are two theories for the mechanism of blood flow generation from chest compressions; (i) the cardiac pump theory—which suggests that the heart is squeezed between the breast-bone and the backbones—and (ii) the thoracic pump theory—where the whole chest functions as a pump due to pressure changes within the chest generated by the chest compressions. The clinical effect is most likely varied combinations of the two.

U.S. Pat. No. 6,398,745 and US 2012/191025 are examples of a known type of chest compression device where a belt around the patient's chest is tightened and relaxed by a belt-tightening spool and electric motor. Published randomized clinical outcome studies so far have not shown a clear improvement in patient survival with a device based on this principle.

US 2003/181834 describes a chest compression device with a plate positioned behind the patient's back and a two-legged front part that can be attached to the back plate. The front part includes a chest compressor which exerts pressure on the breastbone. The arrangement shown in this publication is similar to commercially available chest compression devices, such as the LUCAS™ Chest Compression System manufactured and developed by Jolife AB/Physio-Control of Sweden. U.S. Pat. No. 8,002,720 discloses another similar device.

SUMMARY OF THE INVENTION

Viewed from a first aspect, the present invention provides a chest compression device for cardiopulmonary resuscitation, the device comprising: a support structure for placement about a patient's chest and for holding a chest compressor above a patient's sternum; a chest compressor mounted on the support structure; and lateral chest supports attached to the support structure at points that are laterally either side of the chest when the device is in use, such that the lateral chest supports will apply lateral pressure to the sides of the chest synchronised with a chest compression by the chest compressor.

The device may comprise a horizontal connector between lateral elements of the support structure and being positioned on the chest wall surface when the device is in use. Preferably, the horizontal connector is a plate that is elastic in the anterior posterior dimension. The plate may be used to bind the two lateral supports together. Chest compressions can be delivered on top of this plate.

The application of lateral pressure during chest compressions can increase the blood flow generated by the anterior chest compressions. The lateral pressure from the lateral chest supports also stabilizes the chest to avoid lateral movement of the anterior chest compression device away from the intended compression site on the chest. The use of lateral chest supports hence leads to more effective CPR and is expected to increase patient survival rates. Compared to the belt type devices as described in U.S. Pat. No. 6,398,745 and US 2012/191025 the compression applied to the chest is focussed as lateral pressure on the sides of the chest and vertical pressure on the sternum, instead of an even pressure applied about the circumference of the chest. This is considered to provide an improved blood pumping effect in view of the anatomy of the chest cavity.

The lateral pressure applied to the sides of the chest of the patient is synchronised with a chest compression by the chest compressor, this means that lateral pressure is applied at the same time as when an anterior pressure is applied, i.e. the application of lateral pressure is simultaneous with the application of pressure to the sternum of a patient.

The chest compressor may for example comprise a piston or similar for contacting the chest. An actuator and/or controller device may drive the piston and provide a chest compression with preset timing and pressure or piston stroke. The chest compressor may optionally provide active decompression as well as compression.

The chest compressor which is mounted on the support structure may be a commercially available chest compression device, such as the LUCAS™ Chest Compression System manufactured and developed by Jolife AB/Physio-Control of Sweden.

The chest compressor may be removable from the support structure and/or may be releasably attached to the support structure.

The support structure is preferably arranged to encircle the chest, with elements placed laterally on either side of the chest and hence being used to hold the lateral chest supports. A preferred embodiment comprises a back plate for location beneath a patient's back (when the patient is lying down) and a bridge portion connected to the back plate and passing over the chest. This bridge portion may comprise lateral elements and the horizontal connector plate discussed above. The horizontal connector plate may be arranged for supporting a chest compressor above the sternum. In an alternative arrangement the bridge portion can comprise a structure designed solely for support of a chest compressor above the sternum. For example it may be an arch-shaped structure or similar.

The support structure is preferably a rigid structure which may maintain its shape during chest compressions.

The lateral chest supports may take the form of pads or plates arranged to come into contact with both sides of the chest. The pads may be for passive lateral support of the chest and hence may simply be adjustable to be placed in a fixed location proximate the sides of the chest, whereby lateral support will be provided synchronised with compression of the chest by action of the chest compressor on the sternum. However, it is preferred for the lateral chest supports to be for active lateral compression of the chest, preferably providing lateral compression synchronised with the downward compression from a chest compressor. In preferred embodiments the lateral chest supports are connected to lateral actuators, which may hence be arranged to provide active lateral pressure comprising intermittent compressions synchronised with the vertical chest compressions. The active lateral pressure may have a preset timing corresponding to the timing of the vertical compression of the sternum. The lateral compressions preferably have a preset pressure and/or stroke length applied by the lateral chest supports.

The lateral actuators may be piston type devices as shown, or alternatively they can be any other appropriate actuator, for example gas or liquid filled elements supporting the lateral chest supports or forming a part of the lateral chest supports and being able to move laterally and/or apply lateral pressure by inflation with liquid or gas. The lateral actuators may be arranged to adjust the positioning of the lateral chest supports to fit the patient.

The lateral chest supports may include cushioning and/or an inflatable element such as an inflatable bladder. An inflatable bladder may be arranged to provide the pressure for active lateral compression of the chest. The inflatable bladder may be supported on a plate or pad, which itself may be connected to lateral actuators as discussed above.

In preferred embodiments the lateral chest supports may include additional features including one or more of self adhesive surfaces for permitting active decompression of the chest, defibrillator pads (optionally self adhesive) to permit connection to a defibrillator, and/or a cooling apparatus for inducing hypothermia. The cooling apparatus may take the form of connections to a source of cold air or liquid for passing through a bladder or fluid passage in the lateral chest support. The cooling apparatus may comprise cooling packs for providing cooling via a chemical reaction.

Viewed from a second aspect, the invention provides a method comprising use of the apparatus described above for chest compression in cardiopulmonary resuscitation.

Viewed from a third aspect the invention provides a method of chest compression in cardiopulmonary resuscitation comprising applying lateral compression to both sides of the chest synchronised with chest compressions applied to the sternum.

The method may comprise passive lateral compression applied continuously during (manual or mechanised) compressions but preferably the lateral compression is active and includes an intermittent compression synchronised with the compressions applied to the sternum by a chest compressor device. Active lateral decompression may be applied, for example via adhesive pads fixed laterally to the chest, which may be synchronised with active decompression applied via the sternum.

The method of the third aspect may comprise use of the device of the first aspect and the preferred embodiments thereof, as described above.

These and other features and improvements of the present application and the resultant patent will become apparent to one of ordinary skill in the art upon review of the following detailed description when taken in conjunction with the several drawings and the appended claims.

BRIEF DESCRIPTION OF THE DRAWINGS

Preferred embodiments of the invention will now be described by way of example only and with reference to the accompanying figures in which.

DETAILED DESCRIPTION

Figure 1:
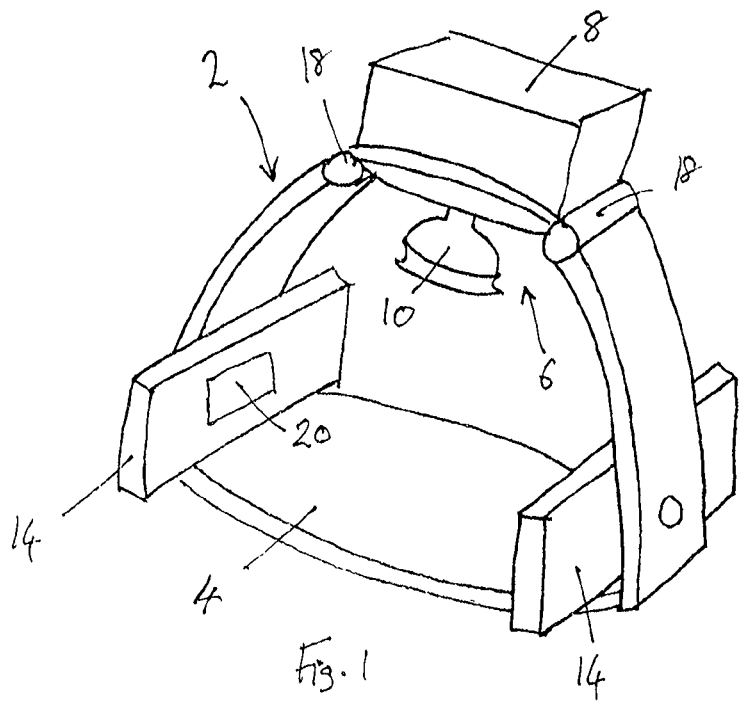
FIG. 1 is a perspective view of a chest compression device with lateral chest supports.
Figure 2:
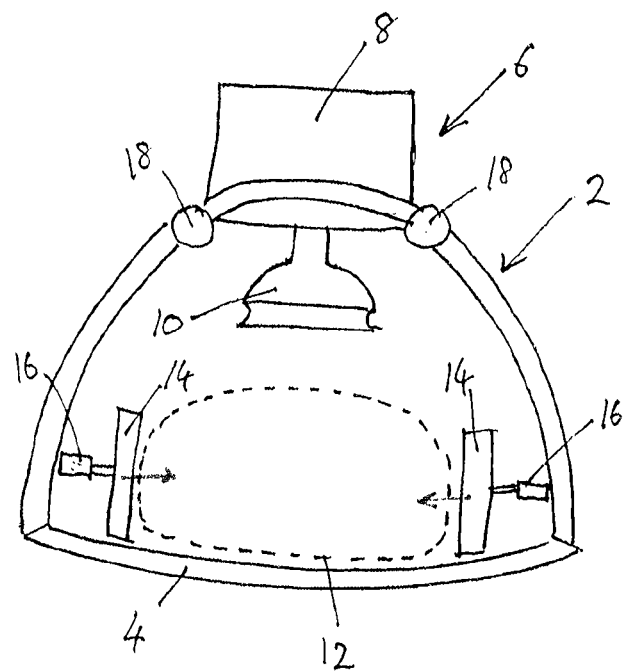
FIG. 2 shows the device in end view, along the longitudinal axis of the body, with the lateral chest supports moved laterally inwards.

The main features of the chest compression device, including the piston arrangement for compressing the chest, can be similar to those found in known products such as the LUCAS™ Chest Compression System manufactured and developed by Joffe AB/Physio-Control of Sweden. Thus, as shown in FIGS. 1 and 2 one preferred embodiment of the device comprises a support structure in the form of an arch 2 over a back plate 4 and supporting a piston device 6, which is to be positioned over the patient's sternum. The patient hence lies on their back with the back plate 4 beneath them and the arch 2 holds the piston device 6 above the chest. The piston device 6 includes an actuator and controller 8 along with a piston 10 that is arranged to compress the chest when driven toward the chest by the actuator. FIG. 2 includes an indication of the positioning of the chest within the chest compression device and shows a schematic cross-section of the torso 12.

The device is further provided with lateral chest supports 14, which are located to be at either side of the patient's chest 12. FIG. 1 shows the lateral chest supports 14 positioned close to the arch 2. FIG. 2 shows the lateral chest supports 14 moved inwardly compared to their position in FIG. 1.

In this embodiment the lateral chest supports 14 take the form of pads arranged to come into contact with both sides of the chest. The pads can be cushioned. Whilst it is possible for the lateral chest supports 14 to apply pressure passively, i.e. simply in relation to deformation of the chest when compressed by the piston device 6, in this exemplary preferred embodiment the lateral chest supports 14 are connected to lateral actuators 16, which are arranged to provide active lateral pressure synchronised with the chest compressions. These lateral actuators can be piston type devices as shown, or alternatively they can be any other appropriate actuator, for example gas or liquid filled elements supporting the lateral chest supports 14 or forming a part of the lateral chest supports 14 and being able to move laterally and/or apply lateral pressure by inflation with liquid or gas.

The lateral chest supports 14 allow the application of a controlled amount of continuous or intermittent lateral pressure in synchronisation with the chest compressions from the piston device 6. This pressure is applied to the chest bilaterally in patients with cardiac arrest when the chest is externally compressed anteriorly by a piston device 6 or similar, with or without active decompression. The pressure from the lateral supports can be continuous or intermittent synchronized with the anterior chest compressions. This application of lateral pressure can increase the blood flow generated by the anterior chest compressions/decompressions in addition to stabilizing the chest to avoid lateral movement of the anterior chest compression device away from the intended compression site on the chest.

In order that the chest compression device will suit patients of different sizes and physical characteristics both the arch structure 2 and the back plate 4 can be adjustable. Hinges 18 allow flexing of the arch 2 and the support structure can be disengaged from the patient by disconnecting the arch 2 from the back plate 4. The lateral actuators 16 of the preferred embodiment can be used to adjust the positioning of the lateral chest supports 14 to fit the patient as well as being used to provide active lateral pressure on the chest.

The preferred embodiment also includes additional features of the lateral chest supports 14 providing potential additional treatment effects. The lateral chest supports 14 include self-adhesive defibrillator pads 20 to permit connection to any defibrillator. This will ensure good skin contact for the pads 20 even when the patient is in a moving vehicle. In addition, the timing of a defibrillation attempt can be controlled towards a set time in the compression/decompression cycle, by interaction of the defibrillator and the controller for the chest compression device. The use of self adhesive pads together with a self adhesive surface of the endplates connected to the bilateral pistons (or other lateral actuators) will also make it possible to actively pull the chest bilaterally and consequently provide active lateral decompression of the chest.

In other embodiments, the lateral chest supports 14, which are shown as pads with pistons 16 in the illustrated preferred embodiment, can alternatively be applied with pistons connected to a solid endplate or with gas/liquid-filled bladders/cushions/bags towards the bilateral surfaces with the amount of gas/liquid continuously controlled by an electronic device. Hydraulic or inflatable systems can be used for lateral adjustment of the lateral chest supports 14 so that they fit the patient and/or for active compression of the chest with lateral pressure.

Figure 3:
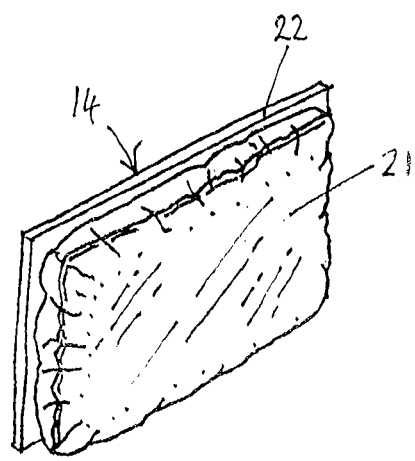
FIG. 3 shows an alternative lateral chest support.

FIG. 3 is an example illustration of a lateral chest support 14 with an air or gas filled inflatable bladder 21. The bladder 21 can be inflated and deflated to apply lateral pressure to the chest. Control of a minimum level of inflation can be used to adjust the position of the outer surface of the bladder 21 and to hence adjust the lateral chest supports 14 to fit patients of different sizes. In this example the bladder 21 is supported by a plate 22 which could in turn be held by a lateral actuator 16 similar to that shown in FIGS. 1 and 2, for lateral movement in addition to the movement provided by inflation and deflation. This lateral movement could be used in the compression of the chest and/or in adjusting the lateral chest supports 14 to fit the patient.

Figure 4:
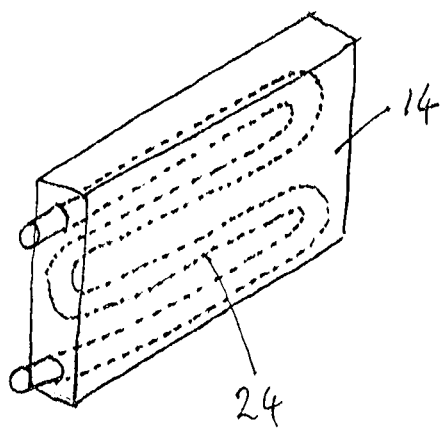
FIG. 4 shows a further alternative lateral chest support.

The lateral chest supports 14 can further be provided with cooling for the chest to be used for hypothermia induction. In the embodiment of FIG. 3 the cooling may be provided by passing cold air/liquid into the bladders 21 and hence the air or liquid passages for inflation of the bladders 21 can also be connected to a source of cold air or liquid. Lateral chest supports 14 in the form of pads as shown in FIGS. 1 and 2 can be provided with fluid passages for cooling air or liquid, for example a serpentine passage 24 as shown in FIG. 4. Cooling to induce hypothermia can hence be achieved by passing cold air/liquid into the bladders or through fluid passages in the lateral chest supports 14. A further alternative cooling mechanism is the use of a chemical reaction inside the bladders 21 or at a cooling pack fixed to the pads of the lateral chest supports 14.

The preferred embodiments are arranged for connection to an external electronic steering module that can control the pressure generating system with active compression decompression (ACD), timing defibrillation attempts, hypothermia induction and so on.

Figure 5:
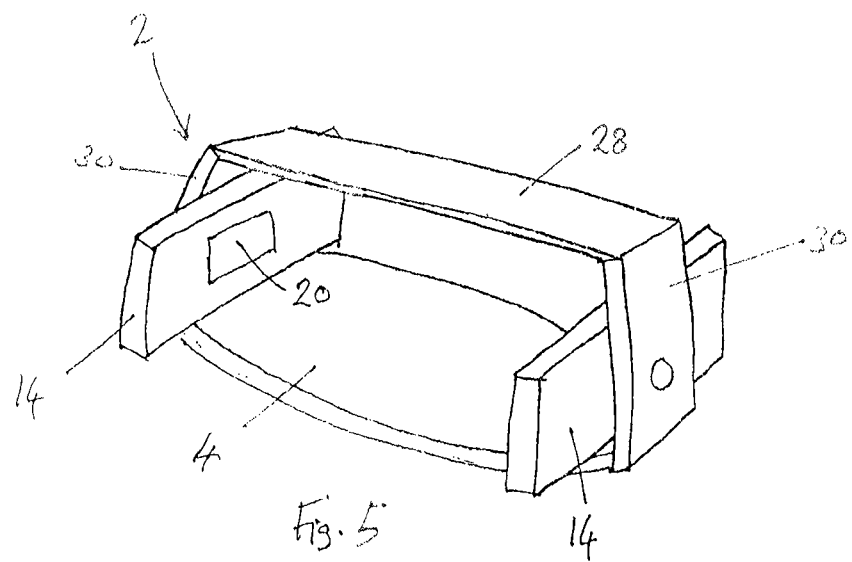
FIGS. 5 and 6 show an alternative embodiment for manual chest compression use.
Figure 6:
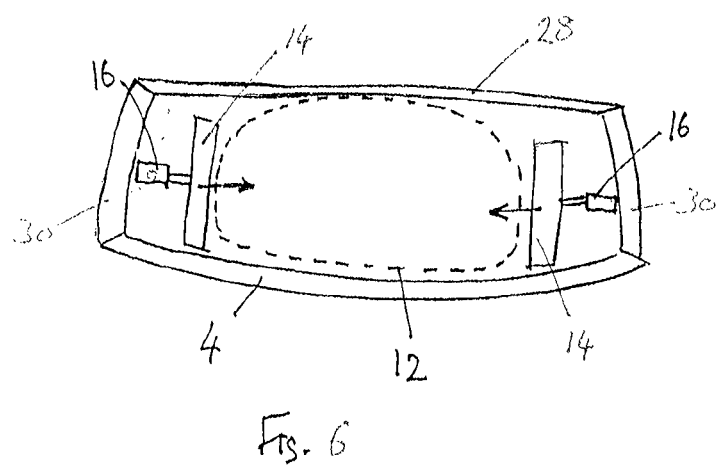
Figure 7:
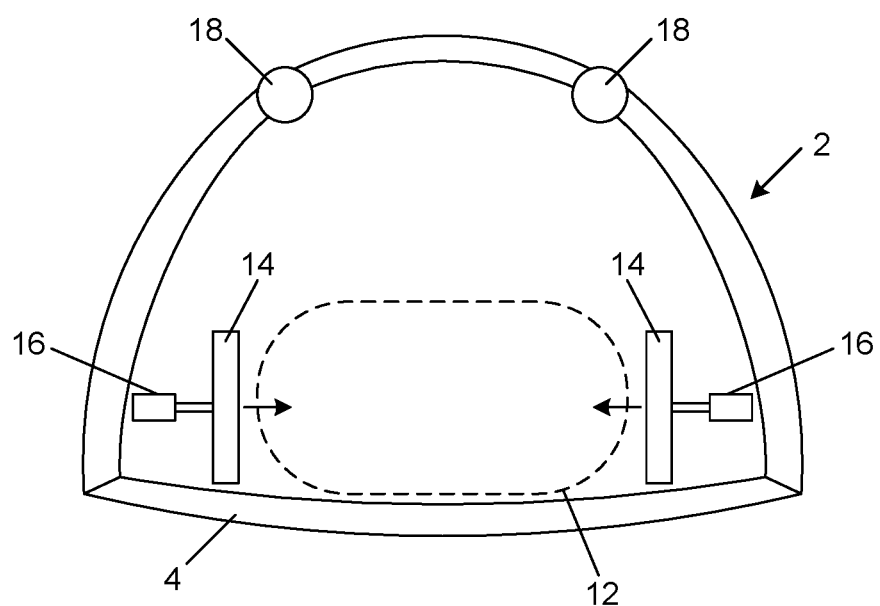
FIG. 7 shows the device of FIG. 2 with a selectively removable piston device.

FIGS. 5 and 6 show an alternative embodiment that is for manual chest compression use. Some elements are similar including the back plate 4 and lateral chest supports 14, along with features relating to the lateral chest supports 14 such as the pistons 16 and defibrillator pads 20. This embodiment differs from that of FIGS. 1 and 2 in that it has a horizontal plate 28 as a part of the support structure 2. The horizontal plate 28 is held on lateral elements 30, which also hold the lateral chest supports 14. In this way the support structure 2 forms a bridge over the back plate 4. The horizontal plate 28 is flexible and permits manual compressions to be applied to the sternum, with lateral pressure being provided synchronised with the manual compressions by the lateral chest supports 14. In the simplest arrangement the lateral pressure will be passive, although of course flexing of the horizontal plate 28 will shorten the distance between the lateral elements 30 and hence some small simultaneous active lateral compression will be applied by the flexing of the device. It is however possible to also allow for active lateral pressure by means of an actuator such as the pistons 16. With this feature the lateral pressure may be actuated in response to anterior chest compressions, for example by means or a pressure or contact sensor in the horizontal plate 28.

The embodiment of FIGS. 5 and 6 can also be adapted to have features as shown in FIGS. 3 and 4, if required.

The present invention was tested on pigs and details of these tests and the results are set out below. Specifically, the haemodynamic performance with and without bilateral thoracic support using a piston based chest compression device was explored in a porcine model of ventricular fibrillation (VF).

Materials and Methods

The experiments were conducted in accordance with "Regulations on Animal Experimentation" under The Norwegian Animal Welfare Authority Act and approved by Norwegian Animal Research Authority (Registration Number FOTS 3563).

Animal Preparation

Healthy domestic pigs of both sexes (28±2 kg) were fasted over night with free access to water. They were sedated in the pen with intramuscular ketamine (40 mg $kg^{-1}$) before intravenous catheter insertion into an ear vein. Intravenous (i.v.) anaesthesia was induced with fentanyl (8 µg $kg^{-1}$) and propofol (3 mg $kg^{-1}$), and maintained with infusions of fentanyl (30-40 µg $kg^{-1}$ $h^{-1}$) and propofol (10-20 mg $kg_{-1}$ $h^{-1}$). The pigs were orally intubated in a prone position and mechanically ventilated (Datex-Ohmeda S/5, GE Healthcare Inc., Waukesha, Wis., USA) with oxygen supplemented air (24-30%) at a positive end-expiratory pressure (5 mmHg). The minute ventilation was adjusted to end-tidal carbon dioxide ($EtCO_2$) 5-6 kPa, measured by a gas monitor ($CO_2$ SMO Plus!, Respironics Novametrix Inc., Wallingford, Conn., USA) inserted into the ventilation circuit.

The pigs were then placed supine in a U-shaped crib with the limbs secured to prevent displacement of the chest during CPR. Physiological saline (33 ml $kg^{-1}$ $h^{-1}$) was continuously infused i.v. and urine output drained through a cystostoma. Temperature was measured intra-abdominally and maintained at 38-40° C. with heating pads (Artic Sun, Medivance Inc., Louisville, Colo., USA). Defibrillator pads were placed caudolaterally on the left and craniolaterally on the right side of the thorax, and a defibrillator (E-series, Zoll, Chelmsford, Mich., USA) continuously monitored ECG.

A 7F micro-tip pressure transducer catheter (Model SPC 470, Millar Instruments, Houston, Tex., USA) was inserted through the right femoral artery and advanced to the aortic arch for continuous arterial pressure monitoring. A 5F micro-tip pressure transducer catheter (Model SPC 470, Millar Instruments, Houston, Tex., USA) was advanced to the right atrium via the right external jugular vein for continuous pressure monitoring. Care was taken to keep mean arterial pressure within 65-90 mmHg by fluid infusions and adjusting the fentanyl and propofol infusions. A 7.5 F Swan-Ganz catheter (Edwards Lifesciences, Irvine, Calif., USA) was inserted into the right atrium via the right femoral vein and a fluid filled polyethylene catheter was inserted into the aorta from the right femoral artery, both for blood gas monitoring and the former to measure cardiac output by thermodilution technique. All visible branches of the left common carotid artery, except the internal carotid artery were ligated, and an ultrasound flow meter probe (Model 3SB880, Transonic Systems Inc., Ithaca, N.Y., USA) was applied for continuous blood flow measurements. All invasive catheters were introduced with cut-down technique.

A craniotomy and duratomy were performed approximately 10 mm anterior to the coronal suture and 15 mm to the left of the sagittal suture. A laser Doppler flowmetry probe (Model 407, Perimed AB, Stockholm, Sweden) was placed on the cerebral cortical surface. Care was taken to avoid placing the probe directly over visible vessels, and it was held in place at the cortical surface by a probe holder (Model PH 07-4, Perimed AB, Stockholm, Sweden) secured with dural sutures. Readings were collected as arbitrary perfusion units that reflect volume flow in the part of the cerebral cortex just below the probe. A burr hole was made on the right side and a 5F micro-tip pressure transducer catheter (Model SPC 470, Millar Instruments, Houston, Tex., USA) was inserted to measure intracranial pressure.

Pressure and flow signals were collected using a PC-based real-time data collection system (NI SCXI-1000, NI PCI-6036E, National Instruments Company, Austin, Tex., USA) supported by VI logger (National Instruments Company, Austin, Tex., USA).

Ventilation data including tidal volume, respiration rate and airway pressures were recorded from the $CO_2$ SMO Plus monitor.

At the end of the experiment the pigs were given a massive dose of propofol and potassium chloride intravenously, and cessation of circulation and heart activity was verified. Autopsies were thereafter performed to verify catheter positions and to check for thoracic or abdominal compression injuries.

Mechanical CPR

Chest compressions were delivered with a commercially available mechanical chest compression device, LUCAS™2 (Jolife AB/Physio-Control Inc., Lund, Sweden). Chest compressions were given according to ERC and AHA 2010 CPR guidelines at the lower half of the sternum with a depth of 53±2 mm for anteroposterior height above 18.5 cm, a rate of 102±2 $min^{-1}$ and a compression/decompression duty cycle of 50%. The device allows free chest recoil between compressions. The anteroposterior diameter of the pigs was measured at the compression point prior to intervention.

Experimental Protocol

After completion of surgery, blood gases, baseline haemodynamic and ventilatory variables were registered after a short stabilization period. Propofol and fluid infusions as well as ventilation were discontinued, and ventricular fibrillation (VF) was induced by advancing an electrode through a thoracic cutdown to the epicardium (30V 2.5 A DC for 3 s). Cardiac arrest was confirmed by ECG and blood pressure changes. After 120 s of untreated VF, mechanical chest compressions were given for 30 s with interposed bag-valve ventilations at 10 $min^{-1}$. The vertical position of the compression piston was adjusted to a new zero position to correct for initial changes in chest configuration.

The intervention consisted of three periods of three minutes duration each with lateral or no lateral support to the chest in a cross-over randomised setup with identical configuration in the first and third periods. Randomisation was done prior to VF induction by drawing from identical envelopes containing the intervention sequence. The design was balanced to ensure equal numbers of the two different directions of interventions.

Lateral support was achieved using inflatable bags (Statcorp Medical, Jacksonville, Fla., USA) supported by a rigid structure. The bags were connected to a $CO_2$-inflator (Richard Wolf Gmbh, Knittlingen, Germany), and the pressure controlled with a digital manometer and a clamplike device. Pressure measured in inflatable bags was 20 cm $H_2O$ in the group "Lateral support" (L) and 60 cm $H_2O$ in the group "Extreme lateral support" (E).

Measurements

Variables measured were arterial pressure, right atrial pressure, cardiac output, carotid blood flow, cerebral cortical blood flow, intracranial pressure, end-tidal $CO_2$, arterial and central venous blood gases. All haemodynamic variables were recorded continuously throughout the experiment (1000 Hz). Reported hemodynamic and ventilatory data were based on the last minute of each of the three consecutive intervention periods, while blood samples were drawn during the second minute of each intervention period. Primary outcome variable was coronary perfusion pressure (CPP) calculated as the difference between aortic and right atrial pressure in the decompression phase. Secondary outcome variables were carotid blood flow, cerebral cortical blood flow (CCBF), and cardiac output.

Statistical Analysis

In each pig the mean value from the first and third intervention periods (with identical interventions) was compared to the value from the second intervention period. All variables are reported as mean±standard deviation (SD) when normality tests were passed and compared with paired Student's t-test using SPSS v19 (SPSS Inc., Chicago, Ill., USA). Differences are presented as mean difference with 95% confidence interval. A p-value of less than 0.05 was considered significant. Power analysis indicated that detecting a 5 mmHg CPP difference with alpha 0.05 with the empirical knowledge of variations in our model, required ten paired comparisons to have a power of 0.9.

Results

One of the twenty pigs was excluded due to a right atrial lesion with subsequent haemothorax. Animal characteristics before induction of VF are shown in Table 1. Return of spontaneous circulation (ROSC) was obtained in 13 pigs, 5 with lateral support and 8 with extreme lateral support. Post-mortem examinations confirmed correct position of all catheters and revealed no thoracic or abdominal compression injuries apart from the atrial lesion described above.

Peak inspiratory pressure increased with extreme bilateral pressure. Due to technical error the ventilation data from the moderate bilateral support group were lost in 4 of 9 animals and in 1 of 10 in the extreme support group.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

TABLE 2

|  | Lateral support | | | | Extreme lateral support | | | |
| --- | --- | --- | --- | --- | --- | --- | --- | --- |
|  | Control | Intervention | Difference (95% CI) | P-value | Control | Intervention | Difference (95% CI) | P-value |
| Mean Aortic Pressure (mmHg) | 31 ± 6 | 35 ± 7 | 4 (1,7) | 0.02 | 34 ± 11 | 45 ± 8 | 11 (6, 16) | <0.01 |
| Mean Right Atrial Pressure (mmHg) | 37 ± 10 | 43 ± 15 | 6 (1, 11) | 0.05 | 49 ± 12 | 55 ± 10 | 6 (0, 11) | 0.08 |
| Coronary Perfusion Pressure (mmHg) | 13 ± 3 | 14 ± 4 | 2 (0.4, 3.1) | 0.03 | 13 ± 3 | 18 ± 3 | 5 (2, 8) | 0.02 |
| Intracranial Pressure (mmHg) | 12 ± 5 | 15 ± 6 | 4 (2, 5) | <0.01 | 18 ± 3 | 29 ± 5 | 11 (9, 13) | <0.001 |
| Mean Oesophageal Pressure (mmHg) | 9 ± 9 | 9 ± 9 | 0.5 (0.1, 0.8) | 0.02 | 6 ± 3 | 6 ± 8 | 0.2 (−0.6, 1) | 0.6 |
| Mean Cerebral perfusion pressure (mmHg) | 15 ± 5 | 16 ± 7 | 1 (−1, 4) | 0.3 | 17 ± 12 | 17 ± 9 | 0 (−4, 4) | 0.9 |
| Mean Carotid Artery Flow (mL/min) | 27 ± 11 | 30 ± 12 | 3 (0.2, 5.2) | 0.07 | 28 ± 5 | 35 ± 7 | 8 (1, 16) | 0.07 |
| Cerebral cortical blood flow (fraction of baseline value) | 0.6 ± 0.4 | 0.6 ± 0.3 | 0 (−0.1, 0.1) | 0.98 | 0.4 ± 0.3 | 0.4 ± 0.3 | 0 (−0.1, 0.1) | 0.8 |
| Cardiac output (l/min) | 1.2 ± 0.2 | 1.3 ± 0.2 | 0.1 (−0.1, 0.2) | 0.2 | 1.2 ± 0.1 | 1.5 ± 0.2 | 0.2 (0.1, 0.4) | 0.02 |
| ET CO2 (kPa) | 3.2 ± 1.0 | 3.1 ± 1.1 | 0 (−0.2, 0.2) | 0.96 | 3.5 ± 0.4 | 3.4 ± 0.5 | −0.1 (−0.5, 0.3) | 0.6 |
| Respiratory measurements (n = 5 and 9, respectively) | | | | | | | | |
| # breaths per min (median and range) | 10 (6.5-19) | 10 (3-11) | 0.2 (−2, 2) | 0.8 | 10 (9.5-11) | 10 (9.5-11) | 0 (−0.3, 0.2) | 0.7 |
| Peak airway pressure (cm H2O) | 46 ± 5 | 50 ± 4 | 5 (0.1, 9.0) | 0.1 | 50 ± 6 | 67 ± 7 | 17 (12, 23) | <0.001 |

TABLE 1

| Baseline characteristics of the 19 animals included in the study. | |
| --- | --- |
| Weight (kg) | 28.7 ± 1.6 |
| A-P diameter (cm) | 19 ± 0.5 |
| Temperature (° C.) | 39 ± 1 |
| Cardiac output (L/min) | 3.3 ± 0.5 |
| Mean Aortic pressure (mmHg) | 88 ± 17 |
| Mean Right atrium pressure (mmHg) | 5 ± 3 |
| Common carotid blood flow (mL/min) | 52 ± 13 |
| Cerebral cortical blood flow (AU) | 494 ± 243 |
| End-tidal $CO_2$ (kPa) | 6.0 ± 0.3 |
| Arterial blood gases | |
| $PaCO_2$ (kPa) | 5.6 ± 0.5 |
| PaO2 (kPa) | 11.7 ± 3.9 |
| pH | 7.4 ± 0.04 |
| BE (mmol/L) | 1.2 ± 1.8 |

Baseline data given as mean ± standard deviation.
AU; arbitrary units.

Pressures and Flows During CPR

Pressures and flows measured during CPR are shown in Table 2. Aortic pressure increased with both levels of bilateral thoracic support compared to the control period with a parallel non-significant trend for right atrial pressure. This caused increased coronary perfusion pressure in both groups compared to control. Cardiac output increased with extreme bilateral support, with no change from control with the lower support pressure. End-tidal $CO_2$ was not influenced by the interventions.

Intracranial pressure increased with both levels of increased lateral pressure compared to the control period without affecting carotid and cerebral cortical blood flows. There was a trend towards higher carotid blood flow with both levels of lateral support (p=0.07).

CONCLUSION

Two levels of lateral support during piston based mechanical chest compressions were tested and it was found that there was an increased coronary perfusion pressure and cardiac output with increasing level of lateral support. There was a concomitant increase in right atrial pressure, intracranial pressure and peak airway pressure, that should have compromised both cerebral flow and cardiac output, but these effects were not discernible in the experiment.

We claim:

1. A chest compression device for cardiopulmonary resuscitation, the device comprising:
   a support structure configured to be placed about a patient's chest and to hold a chest compressor above the patient's chest;
   a chest compressor mounted on the support structure; and
   lateral chest supports attached to a chest facing side of the support structure at points that are laterally on either side of the chest when the device is in use, wherein the lateral chest supports are coupled to one or more lateral actuators configured to apply lateral pressure to the sides of the patient's chest by actively moving the lateral chest supports towards one another to provide at least an active lateral compression that is synchronized with at least a chest compression by the chest compressor.

2. A device as claimed in claim 1, wherein the chest compressor is arranged to provide active decompression as well as compression.

3. A device as claimed in claim 1, wherein the one or more lateral actuators comprise pistons and/or gas or liquid filled elements.

4. A device as claimed in claim 1, wherein one or more of the lateral chest supports include an inflatable element.

5. A device as claimed in claim 4, wherein the inflatable element includes an inflatable bladder.

6. A device as claimed in claim 1, wherein the lateral chest supports each comprise an inflatable bladder arranged to provide pressure for active lateral compression of the chest.

7. A device as claimed in claim 1, wherein the lateral chest supports comprise adhesive surfaces for permitting active decompression of the chest.

8. A device as claimed in claim 1, wherein the lateral chest supports comprise defibrillator pads for connection to a defibrillator.

9. A device as claimed in claim 1, wherein the lateral chest supports comprise a cooling apparatus configured to induce hypothermia.

10. A device as claimed in claim 9, wherein the cooling apparatus includes connections to a source of cold air or liquid to introduce cold air or liquid into a bladder or fluid passage in one or more of the lateral chest supports.

11. A device as claimed in claim 9, wherein the cooling apparatus comprises cooling packs operable via a chemical reaction.

12. A device as claimed in claim 1, wherein the support structure comprises a horizontal connector configured to be positioned on the patient's chest when the device is in use.

13. A method of chest compression in cardiopulmonary resuscitation comprising:
   providing a piston-driven chest compressor to deliver a chest compression to a patient's chest;
   providing a first lateral chest support and a second lateral chest support;
   causing the chest compressor to be driven to deliver the chest compression;
   causing the first lateral chest support and the second lateral chest support to be driven by one or more lateral actuators to deliver respective first and second lateral compressions to the sides of the patient's chest by actively moving the lateral chest supports towards one another, wherein each lateral compression is synchronized with the chest compression.

14. A method as claimed in claim 13, wherein the first and second lateral compressions are intermittently synchronized with the chest compression.

15. A method as claimed in claim 13, further comprising causing the first lateral chest support and the second lateral chest support to be driven to deliver active lateral decompression.

16. A chest compression device for cardiopulmonary resuscitation of a patient, the device comprising:
   a back plate configured to be positioned posterior to a chest of the patient;
   a support structure configured to partially encircle the chest of the patient and further to be coupled to the back plate at a first end and a second end of the support structure; and
   an electrically-driven piston device configured to compress the chest of the patient, the piston device being supported by the support structure and configured to be removable from the support structure; and
   lateral chest supports attached to a chest facing side of the support structure at points that are laterally on either side of the chest when the device is in use, wherein the lateral chest supports are coupled to one or more lateral actuators configured to apply lateral pressure to the sides of the patient's chest by actively moving the lateral chest supports towards one another to provide at least an active lateral compression that is synchronized with at least a chest compression by the chest compressor.

17. The chest compression device of claim 16, in which the piston device is configured to be releasably attached to the support structure.

18. The chest compression device of claim 16, in which the piston device further comprises an actuator configured to drive a piston of the piston device.

19. The chest compression device of claim 16, in which the piston device is further configured to decompress the chest of the patient.

20. The chest compression device of claim 16, in which the support structure is rigid and configured to maintain shape when the piston device compresses the chest of the patient.

21. The chest compression device of claim 16, in which the support structure comprises an arch member.

* * * * *